(12) United States Patent
Tanaka et al.

(10) Patent No.: US 6,613,593 B2
(45) Date of Patent: Sep. 2, 2003

(54) METHOD OF FABRICATING A SEMICONDUCTOR DEVICE

(75) Inventors: Maki Tanaka, Yokohama (JP); Masahiro Watanabe, Yokohama (JP); Kenji Watanabe, Oume (JP); Mari Nozoe, Hino (JP); Hiroshi Miyai, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/942,862

(22) Filed: Aug. 31, 2001

(65) Prior Publication Data

US 2002/0197750 A1 Dec. 26, 2002

(30) Foreign Application Priority Data

Jun. 20, 2001 (JP) .......................................... 2001-185773

(51) Int. Cl.[7] .............................................. G01R 31/26
(52) U.S. Cl. .......................................... 438/16; 250/310
(58) Field of Search ............................. 250/310; 430/30

(56) References Cited

U.S. PATENT DOCUMENTS 6,172,363 B1 * 1/2001 Shinada ...................... 250/310

OTHER PUBLICATIONS

D Kahng, T.A. Shankoff, T.T. Sheng and S.E. Haszko; "A Method for Area Saving Palnar Isolation Oxides Using Oxidation Protected Sidewalls", Nov. 1980, J Electrochem. Soc.: Solid State Science and Technology; p. 2468–2471.*

* cited by examiner

Primary Examiner—John F. Niebling
Assistant Examiner—Andre' C Stevenson
(74) Attorney, Agent, or Firm—Antonelli, Terry, Stout & Kraus, LLP

(57) ABSTRACT

A method and apparatus for inspecting a semiconductor device in which failure occurrence conditions on a whole wafer are estimated by calculating the statistic of potential contrasts in pattern sections from sampled images to implement higher throughput, and defective conditions of a process are detected at an early stage with the help of time series data of the estimated result.

18 Claims, 19 Drawing Sheets

□ NORMAL
▨ FAILURE RATE BELOW 50%
▦ FAILURE RATE OVER 50%

LOW PATTERN DENSITY

FIG. 14(b) HIGH PATTERN DENSITY

METHOD OF FABRICATING A SEMICONDUCTOR DEVICE

CROSS-REFERENCE TO RELATED APPLICATION

This application is a division of application Ser. No. 09/942,213 filed on Aug. 30, 2001, by Maki Tanaka et al. entitled "METHOD AND APPARATUS FOR INSPECTING A SEMICONDUCTOR DEVICE".

BACKGROUND OF THE INVENTION

This invention relates to a technique of fabricating a semiconductor device; and, more particularly, the invention relates to a method of fabricating a semiconductor device suitable control of defective conditions which occur in the fabricating processes carried out in a semiconductor device production line.

In a semiconductor device, a conduction failure of contact holes leads to fatal defects including characteristic failures and has a significant impact on yield of the semiconductor device. Such a failure is often caused by changes in production requirements or defective conditions of manufacturing equipment and often invites a large amount of defective units.

Such defective conditions of process are controlled, in general, by a means of periodically checking for changes in pattern geometries with a critical dimension measurement SEM. However, only evaluation of pattern geometries cannot directly inspect conducting state of contact parts.

On the other hand, JP-A No. 2000-58608 etc. have disclosed A method of detecting conduction failures by using brightness of contact parts as well as pattern geometries. This method utilizes a feature of an electron microscope image. Charge-up amount of a pattern by irradiation of electron beams varies depending on the conducting states of contact parts and shows contrast between normal parts and defective parts on a secondary electron image to be detected. With such a method as this, it is possible to inspect electrical characteristics that cannot be checked by a visual check of the external view.

In recent years, wafer inspection apparatus using SEM images has also come to be utilized as has been disclosed in JP-A Nos. 1993-258703 and 2000-208085 and efficient defect inspection has become possible. This kind of apparatus utilizes repeatability of the same patterns containing devices such as cells and chips within the conductor traces and compares images of these patterns to detect defects.

As stated above, a method using SEM images has come into widespread usage as a means of detecting electrical conduction failures of contact windows. However, it requires considerably long time to obtain an SEM image with a high signal-to-noise ratio and high resolution; it takes a few hours to tens of hours to perform inspection of a whole wafer. Therefore, the in-line usage is difficult. In addition, an inspection method of performing comparison of images has a drawback in that, on the quantity occurrence of defects, images of the defects are compared with each other, making an accurate defect inspection difficult.

In addition, all of these inspection methods are intended for defect inspection, so thy cannot predict occurrence of electrical conduction failures. However, since failures caused by changes in production requirements and defective conditions of manufacturing equipment can suddenly be encountered in a large amount and on a massive scale and invite too many wafers with defects at the same time of the occurrence, it is desirable to detect changes in processes.

SUMMARY OF THE INVENTION

This invention provides A method of keeping track of failure occurrence conditions on a whole wafer of interest by using as small area subject to an inspection as possible.

This invention also provides A method of controlling changes in processes to prevent a rash of failures caused by defective conditions of manufacturing equipment.

In this invention, inspection is performed by obtaining charged particle beam images at a desired area on the surface of a wafer, calculating a typical signal amount value typifying the signal amount of charged particle beams emitted by each pattern from the obtained images, and estimating failure occurrence conditions outside the image-obtained area from the statistic of the typical signal amount value. In addition, this invention makes it easier to determine the causes of failures by providing a function for displaying the time series data of section results for each equipment which treated the wafer.

In other words, this invention, in A method of inspecting a wafer on the surface of which the same pattern is repetitively formed, comprises the steps of obtaining a charged particle beam image of a desired area of the wafer by detecting secondary charged particles emitted from the surface of the wafer with irradiation of a focused charged particle beam onto the surface of the wafer, calculating the image feature amount of each pattern within the desired area from the obtained charged particle bean images, computing the statistic of the calculated image feature amount, comparing a preset value to the computed statistic of the image feature amount, and estimating the quality of patterns that have been formed outside the desired area from the result of the comparison.

In addition, this invention, in A method of inspecting a wafer having patterns that have been repetitively formed on the surface of the wafer and have differences in geometries within a chip or interconnecting conditions with a lower layer or in both, comprises the steps of:

obtaining a charged particle beam image of a desired area of a wafer, calculating the image feature amount of each pattern contained in the obtained charged particle beam image from the obtained charged particle beam image, determining the statistic of the image feature amount computed for each pattern type, comparing a threshold that has been preset in association with a pattern type to the statistic that has been computed for that pattern type, and estimating the quality of patterns that have been formed outside the desired area from the result of the comparison.

Furthermore, this invention, in A method of inspecting a wafer on which a plurality of chips with the same pattern of traces are formed, comprises the steps of:

obtaining a charged particle beam image of a specific place on one of the plurality of chips by focusing charged particle beams onto the specific place, estimating the failure occurrence conditions of the remaining chips on the wafer with the help of inspection data obtained from the charged particle beam image of the specific section, determining the distribution of the estimated failure occurrence conditions of the chips on the wafer, and outputting information of the distribution of the failure occurrence conditions on the wafer to be inspected.

This invention, in A method of manufacturing a semiconductor device, comprises the steps of:

obtaining a charged particle beam image of a preset place by irradiating a focused charged particle beam onto the preset place on a wafer that has been operated upon in given processing stages, repeating this step for a plurality of wafers that have been operated upon in the given processing stages, and comparing the brightness of the charged particle beam images of the specific places which have sequentially been obtained from the plurality of wafers with the preset values to control changes in process of the given processing stages.

This invention, in A method of manufacturing a semiconductor device, comprises the steps of determining the distribution of failures over a wafer from a charged particle beam image obtained by irradiating a focused charged particle beam onto a plurality of preset sections on a wafer that has been operated upon in given processing stages, and controlling changes in process of the given processing stages on the basis of verifications in distribution of failures from wafer to wafer.

This invention, in A method of manufacturing a semiconductor device by processing it through a plurality of processing stages, comprises the steps of:

obtaining a charged particle beam image of a preset section by irradiating a focused charged particle beam onto a preset place on a given wafer after the given wafer has been operated upon in each of the plurality of processing stages, repeating the step for each of the plurality of processing stages, and monitoring the brightness of the charged particle beam images obtained for each processing stage to control the plurality of processing stages.

These and other objects, features and advantages of the invention will be apparent from the following more particular description of preferred embodiments of the invention, as illustrated in the accompanying drawings.

BRIEF DESCRIPTION OF THE DRAWINGS

FIG. 14(a) and FIG. 14(b) are both plane views of semiconductor chips showing contact window patterns;

DESCRIPTION OF THE PREFERRED EMBODIMENTS

Figure 1:
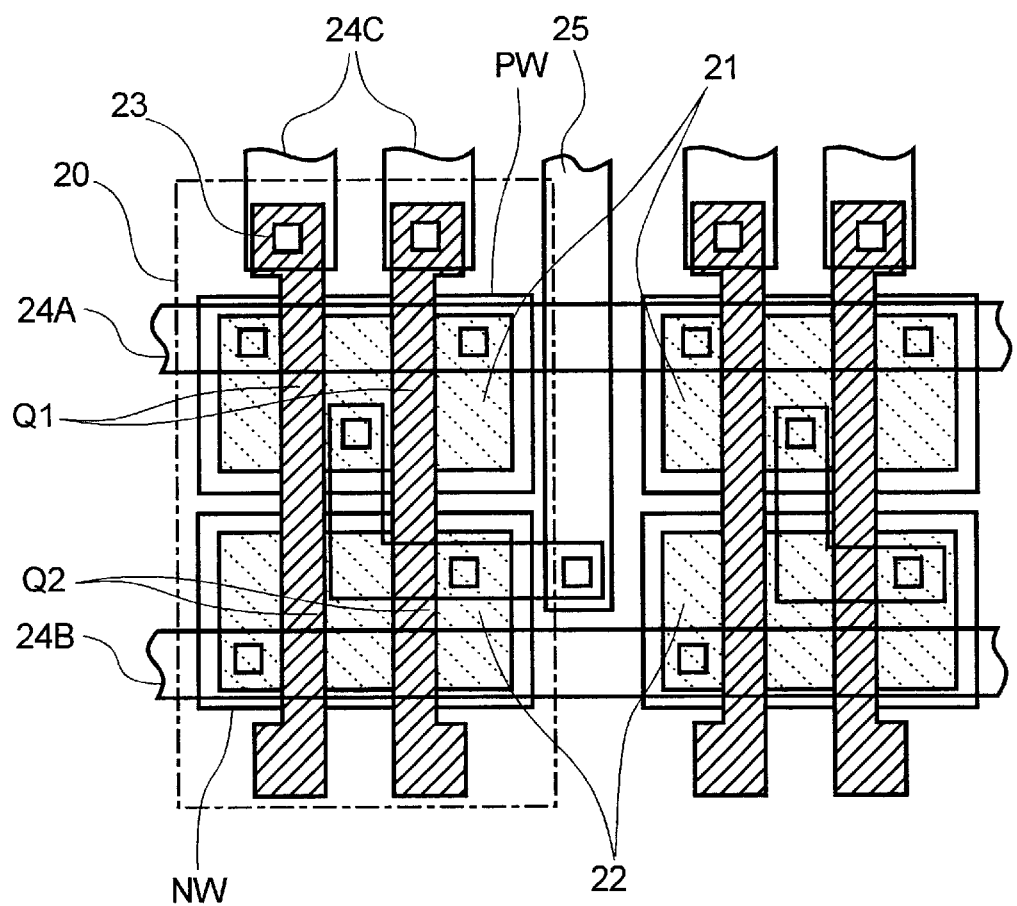
FIG. 1 is a plane view of a semiconductor device.
Figure 2:
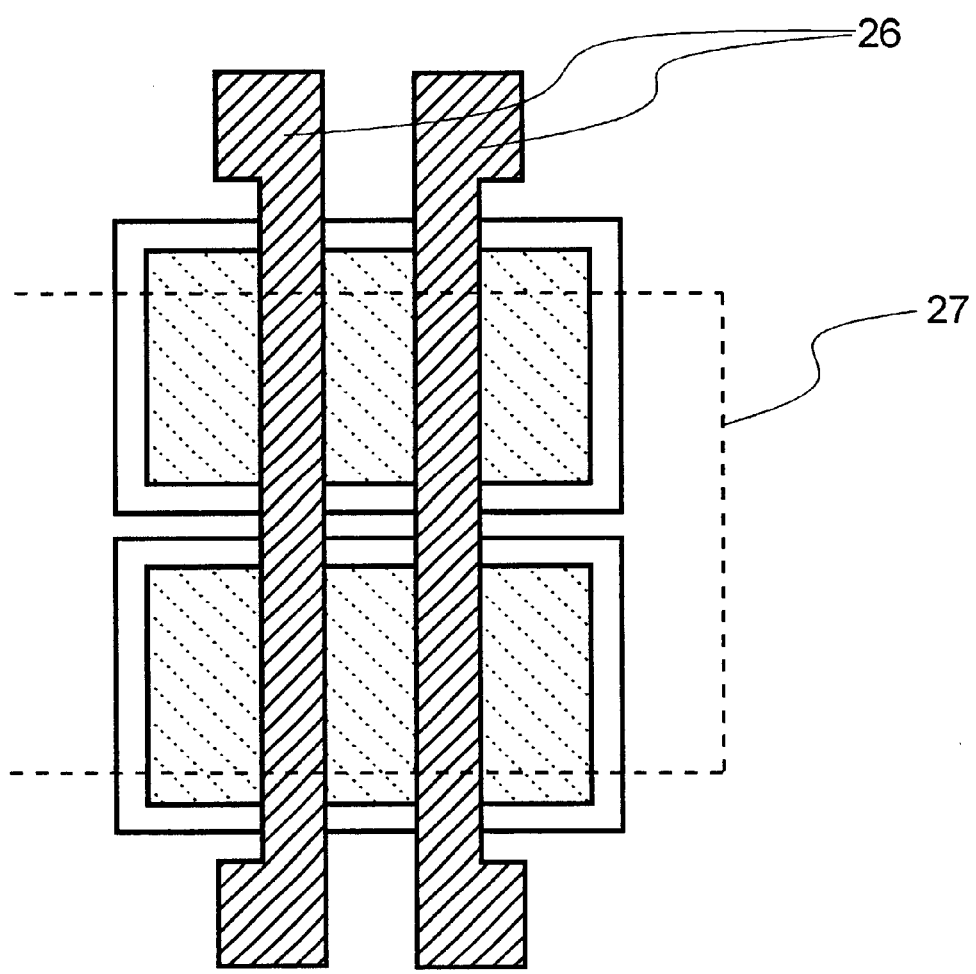
FIG. 2 is a plane view of a semiconductor device.

FIG. 1 shows an example of a logic unit of a semiconductor device which is an object sample of the invention. This logic unit consists of a unit cell 20 enclosed with a phantom line in a plane view shown in FIG. 1. The unit cell 20 consists of two pieces of n-channel MOS chip Q1 and two pieces of p-channel MOS chip Q2. The n-channel MOS chip Q1 is formed on an n-type region 21 in the surface of a p-WELL region PW formed on a substrate, and the p-channel MOS chip Q2 is formed on a p-type region 22 in the surface of an n-WELL region NW, respectively. Here, a plane view of a unit cell before different types of traces 24A, 24B, 24C, and 25 are formed on it is shown in FIG. 2. Reference numeral 26 is a polysilicon gate pattern. This unit cell is structured in such a way that 2-input NAND gates and 2-input NOR gate circuits can be formed efficiently by selecting traces to be subsequently added as necessary, and this structure is also extended to the structures connecting a large number of CMOS chips.

Figure 3:
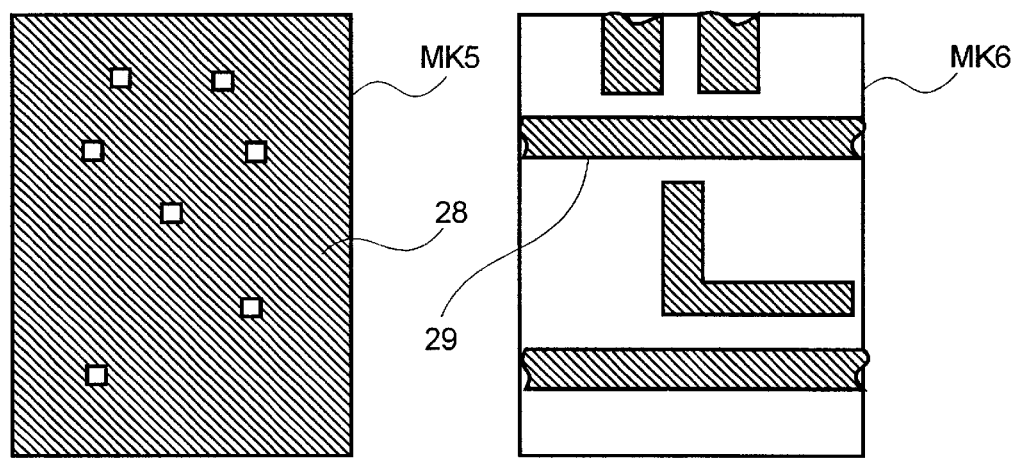
FIG. 3 is a plane view of masks used for exposure.

FIG. 3 shows example masks, which are used to form contact widows and patterns of traces shown in FIG. 2, thereby making a circuit.

These semiconductor devices are fabricated by iteration of a number of pattern-forming processes as shown in FIG.

4. Generally, each pattern-forming process mainly consist of stages of oxidization 30, resist coating 31, exposure 32, developing 33, etching 34, resist stripping 35, and cleansing 36. Unless parameters of fabrication process at each of these stages are optimized, correct trace patterns of a semiconductor device cannot be formed, resulting in occurrence of failed products. These semiconductor devices are electrically analyzed after the completion of the wafer fabrication processes, causes of defects are examined by fail-bit analysis and other methods, and a control against them is performed. However, with such a method, if failures have occurred somewhere in fabrication processes, they cannot be detected until whole processing for the wafer of the product complete. It usually takes tens of days to manufacture a semiconductor device, so a method like this has a drawback in that defective units are produced in a large amount before corrective action is taken.

Figure 4:
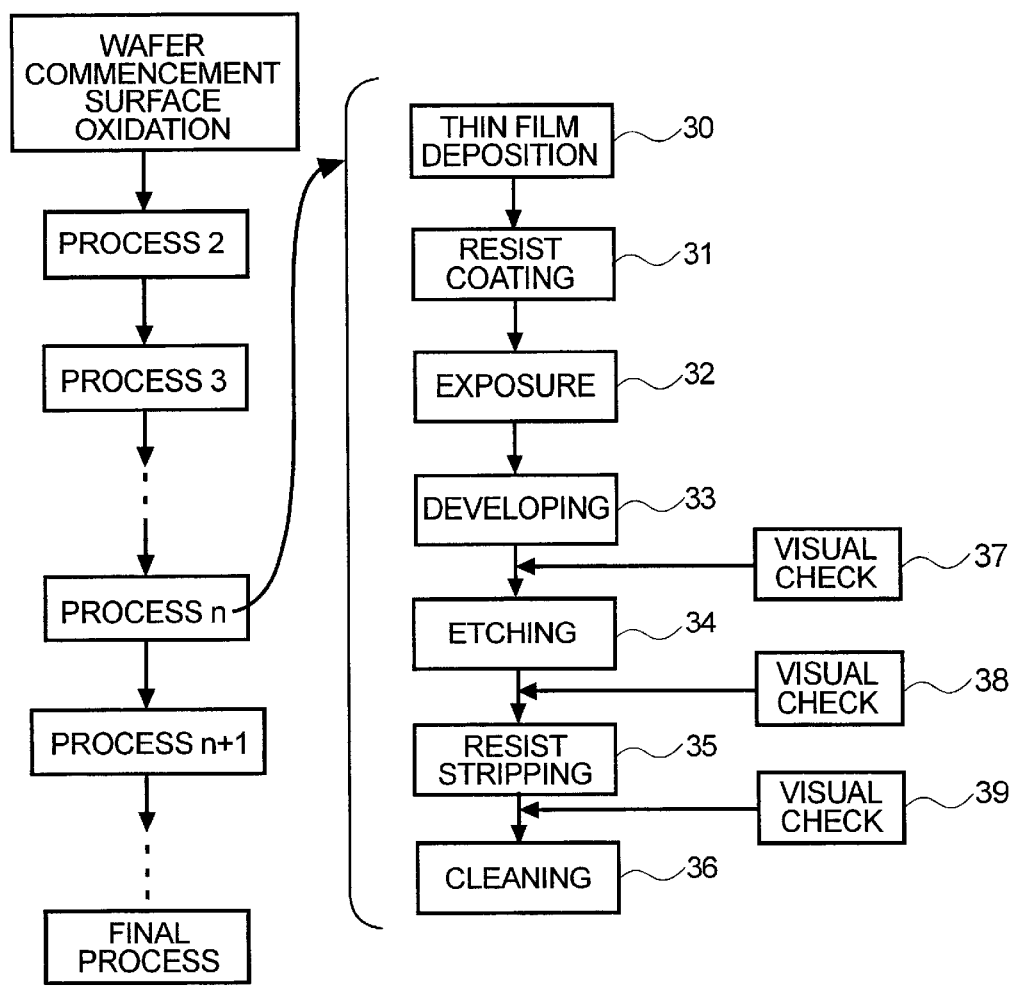
FIG. 4 is a process flow chart showing the processing stages of a semiconductor device.

In contrast to this, if visual checks 37, 38, and 39 are performed in each stage of the fabricating processes as shown in FIG. 4, even for the occurrence of failures caused by defective conditions of equipment, diagnosis and corrective action can be taken at an earlier stage. As a result of this, it becomes possible to reduce the number of defective units, improved production efficiencies, and increase profits.

Failures occurring in these fabricating processes include failures occurring relatively on a random and local basis and failures occurring by defective conditions of fabricating equipment and fluctuations of process parameters. In particular, the latter type of failures might occur in an entire wafer or across several wafers and is prone to be produced in a large amount. It often has a remarkable occurrence distribution.

This invention provides A method of controlling occurrence of failures to the minimum by detecting the latter type of failures at an early stage, determining equipment causing the failures, and taking corrective action. More specific examples of the latter type of failures include resist residues caused by inadequate development and etching, and electrical conduction failures and short circuits caused by failed alignment with lower layer patterns. In addition, this invention provides A method of predicting occurrences of failures by controlling normal levels.

Figure 5A:
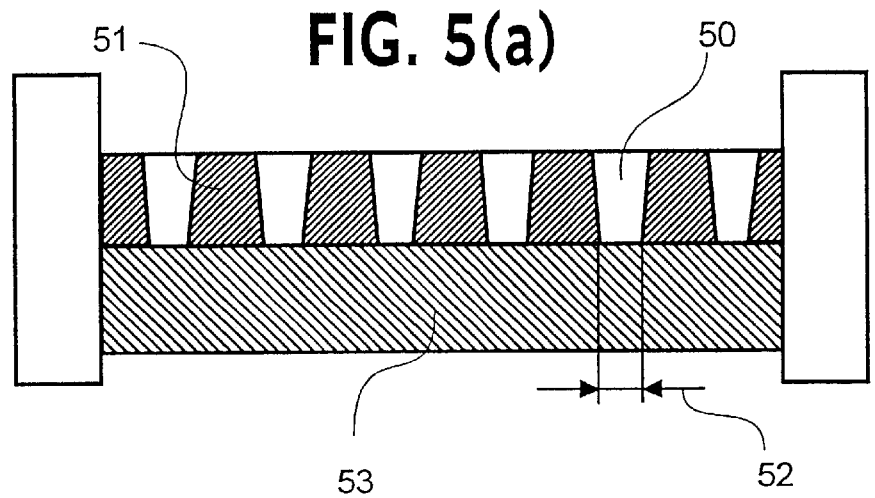
FIG. 5 is a section view of a contact window pattern.
Figure 5B:
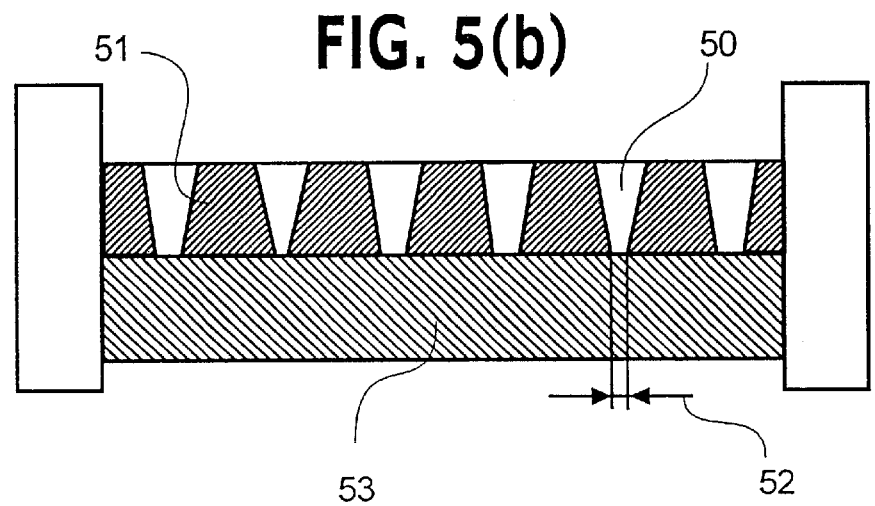
Figure 5C:
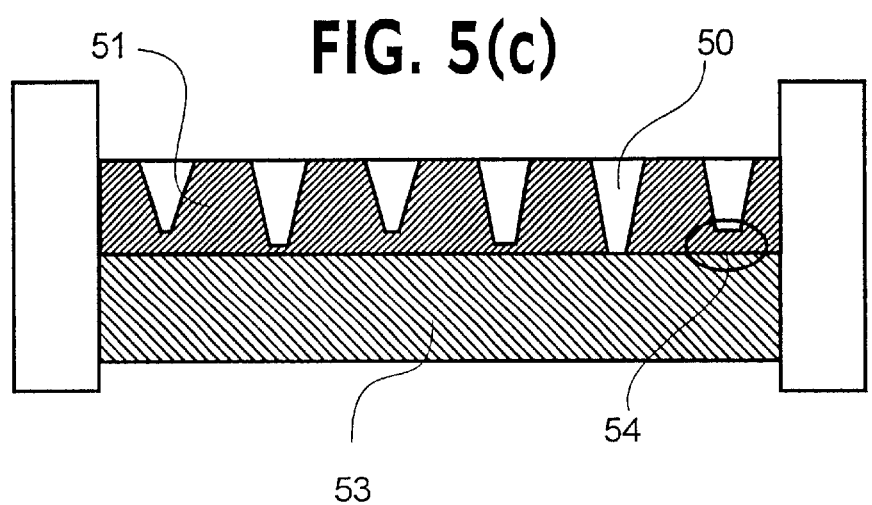

As an example subject, FIG. 5 shows a section view of a contact window pattern where inadequate etching has occurred. Adequate etching time opens a contact window 50 of a normal size as shown in FIG. 5(a), but inadequate etching decreases a diameter of a window bottom 52 as shown in FIG. 5(b), and with over a certain extent, resulting in failures causing high resistance. Further inadequate etching decreases the size of windows with oxide film residue 54 at some spots in the window bottom as shown in FIG. 5(c), causing electrical conduction failures. Lower etch uniformity of etching equipment causes variations of the occurrence rate of such failures within the surface of a wafer. The presence or absence of these conditions can be determined by using electron microscope images.

When the surface of a specimen is scanned with electron beams, secondary electrons are emitted in response to the amount of electrical charges on the surface. Since the amount of electrical charges of the surface of a specimen depends on the electrical characteristics of a pattern formed on the surface of the specimen, evaluating the signal amount of these secondary electrons enables determination of the quality of the formed pattern. Hereinafter, an embodiment using electron microscope images will be described, but it is obvious that the application of other kinds of charged particle beam images such as SIM (secondary ion mass) images of FIB (focused ion beam) produces the same effect.

Figure 6A:
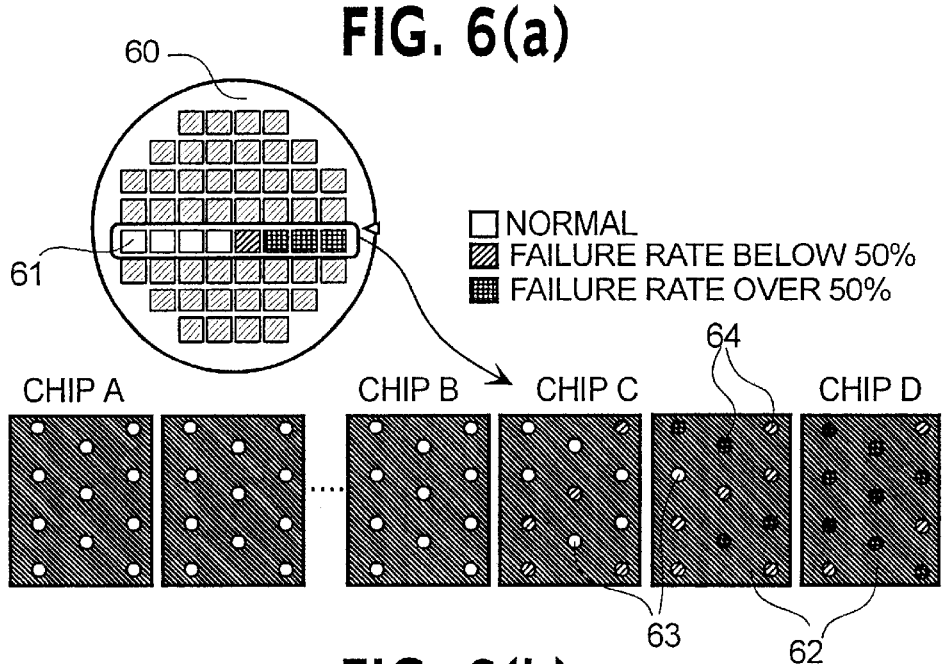
FIG. 6(a) is a plane view of a wafer and chips.
Figure 6B:
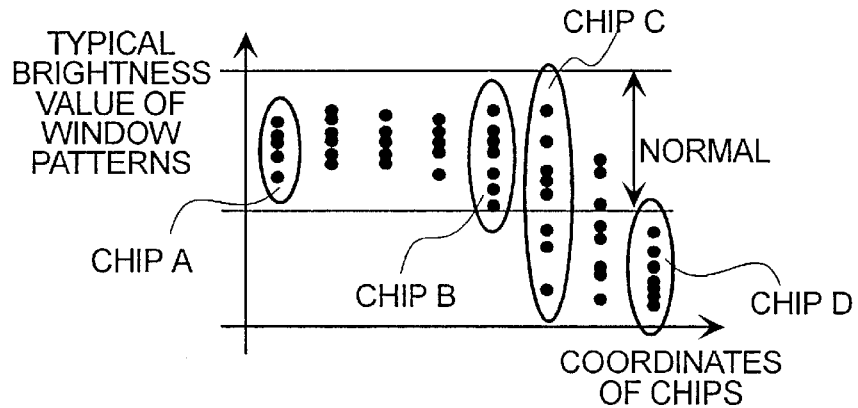
FIG. 6(b) is a drawing showing distribution of the brightness of contact window patterns.
Figure 6C:
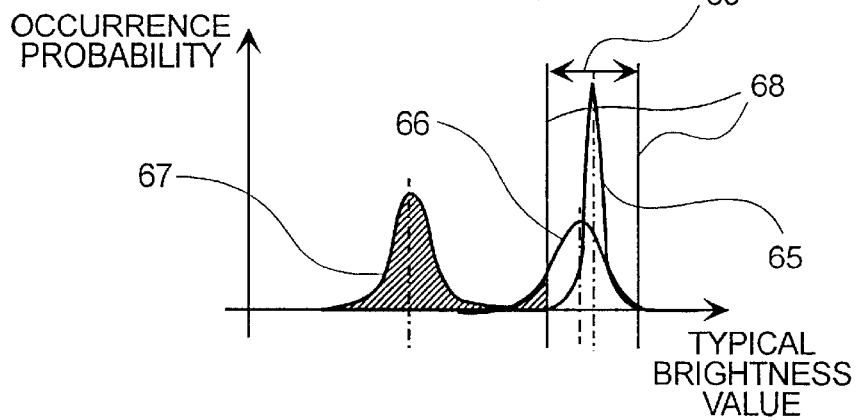
FIG. 6(c) is a drawing showing the relationship between the typical brightness value and probability of the occurrences.
Figure 7:
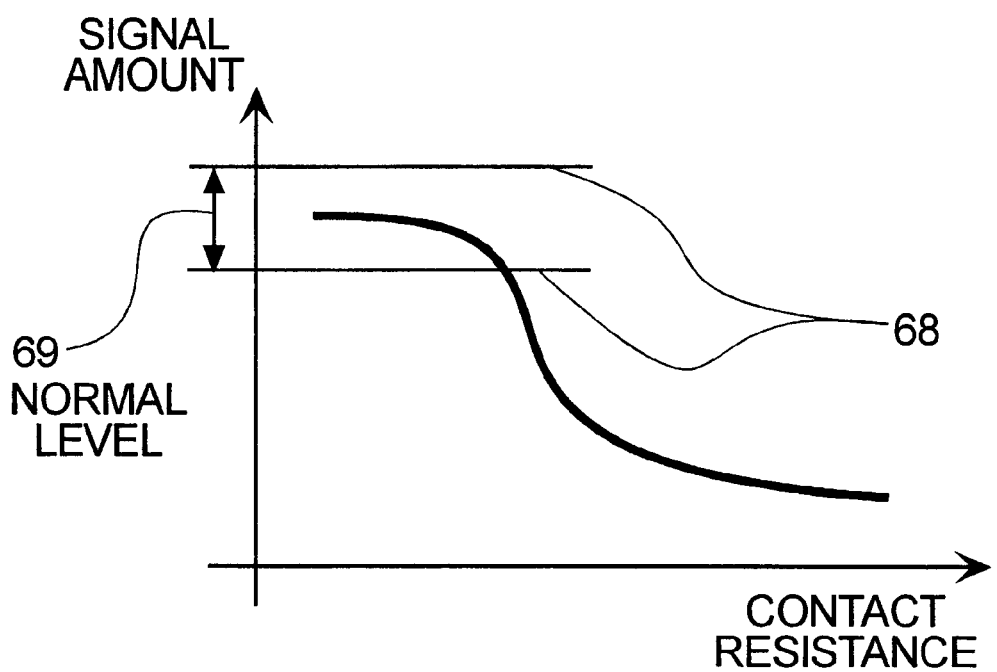
FIG. 7 is a drawing showing the relationship between contact resistance and signal amount.

Referring to FIG. 6 and FIG. 7, a means for detecting electrical conduction failures of contact windows as shown in FIG. 5 will be described. FIG. 6 shows an example of electrical conduction failures caused by inadequate etching, which are gradually increasing toward the notch side of a wafer 60. As shown in FIG. 6(a), if a secondary electron beam image 62 obtained within a given group of chips 61 on the wafer 60 displays a normal section 63 of contact window patterns with high brightness and a failure section 64 of contact window patterns with lower brightness. Current inventions have proposed a method of evaluating the quality of each contact window pattern on the basis of the variations of this brightness. With this method, especially when the relationship between signal amount of secondary electron beams detected from the pattern of a contact window with an electron microscope and contact resistance between the window part and an underlying conductor or thickness of a film residue is known as shown in FIG. 7, a threshold level 68 for evaluating the quality of window patterns can easily be determined from the normal resistance value.

This invention enables estimation of failure occurrence conditions in patterns of contact windows other than those the images of which have been obtained. The brightness of contact window patterns within images obtained for each chip is measured (FIG. 6(b)). Where, the brightness of a window pattern is a typical value indicating the variations of secondary electron amount emitted from the window pattern, such as an average brightness value and a maximum brightness value within the window pattern area. If the average value and distribution of brightness of these window patterns are determined, probability distribution functions 65, 66, and 67 on the assumption of normal (Gaussian) distribution can be determined as shown in FIG. 6(c). Using the relationship between a result of this and a preset threshold level for evaluating the quality of patterns enables estimation of the percentage of failed patterns in a chip from the representative image of one of chips with same pattern. For example, in a chip B shown in FIG. 6, although all windows within the detected image are normal, it can be estimated that there is 20 percent potential of failed window patterns existing in other chips with the same pattern. If results of these evaluations are displayed on a wafer map as shown in FIG. 6(a), failure occurrence conditions can easily be checked.

Current inventions have required quite a long time to detect this kind of failure because they have to obtain electron beam images of an entire wafer before evaluating failures from the difference between the window pattern in an area of interest and window patterns outside the area. In contrast to the method of the current inventions, the method of this invention enables estimation of the presence or absence of failures with the help of smaller number of images of one or a few windows on each chip, saving much inspection time and increasing the frequency of sampling tests.

Figure 8A:
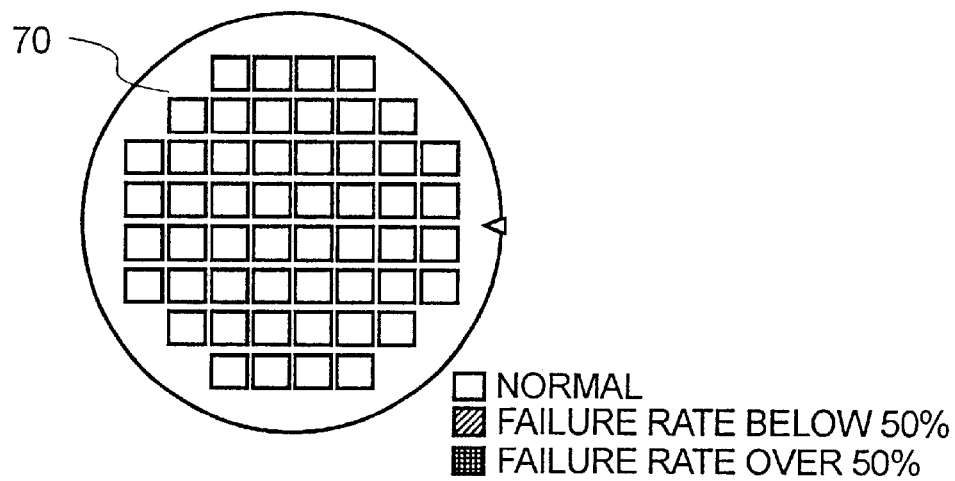
FIG. 8 is a plane view of wafers showing failure occurrence conditions varying with the time of commencement.
Figure 8B:
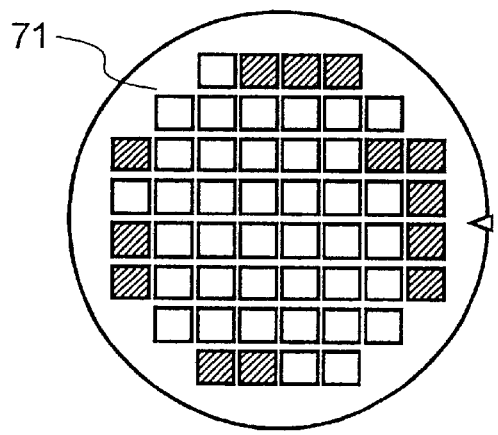
Figure 8C:
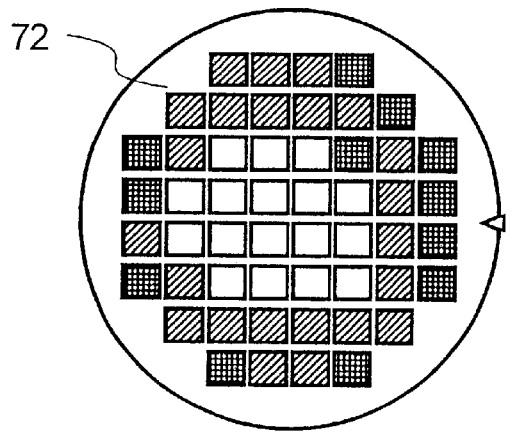

In the example in FIG. 6, failed contact window patterns have practically been detected in chip C and chip D, but failure occurrence can be estimated from the image of chip B. For example, in such a case that the number of failures gradually increases with time of commencement from (a) to (b) and to (c) as shown in FIG. 8, keeping high sampling frequency makes it possible to detect defective conditions and take corrective action during the impact of the failures on the production is small (before the state of FIG. 8(b) or the previous state).

In addition, such a method of current inventions as to detect contrast differences between a pattern of an area of interest and patterns outside the area cannot correctly detect failures if all patterns have failures, while the method of the invention that evaluates the absolute values of the brightness of window patterns implements correct inspections even in such a case.

FIG. 6 shows a method of inspecting only a line of chips for simplicity, but it would be possible to inspect all chips or optionally fewer chips such as those at five positions (up, down, right and left side and center positions). Of course, it would also be possible to increase check positions within a chip. In order to evaluate variations, it is desirable that tens to hundreds of patterns (window patterns in the case of FIG. 6) within a single image can be evaluated. If the sufficient number of patterns cannot be obtained in a single image, several images of other areas on the periphery of the area of interest may be used to perform operations similar to these.

Note that the relationship between the brightness of a window pattern and contact resistance between the window pattern and the underlying conductor has to be determined for every inspection apparatus because it varies with acceleration voltages of electron beams or irradiation parameters such as beam current. A method of determining the control values will be described later in detail.

Figure 9A:
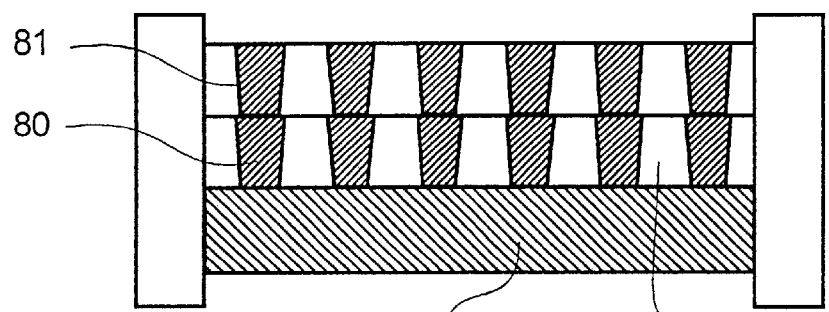
FIG. 9 shows section views of a wafer showing the offset conditions against a lower pattern.
Figure 9B:
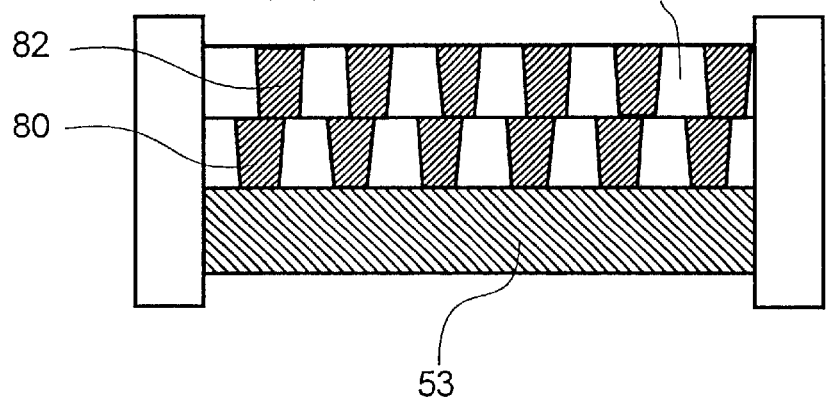
Figure 10A:
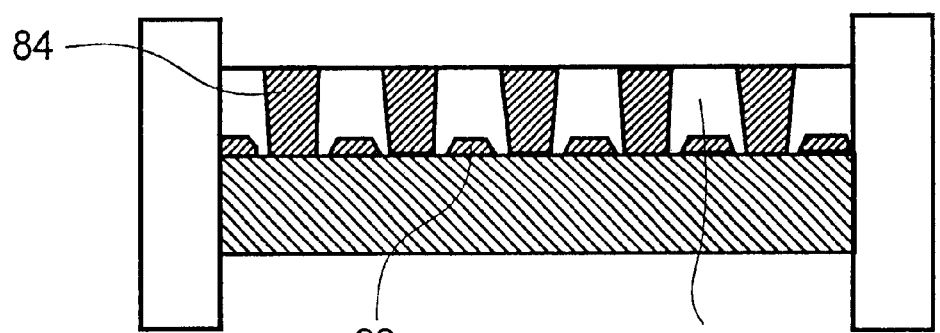
FIG. 10 shows section views of a wafer showing the offset conditions against a lower pattern.
Figure 10B:
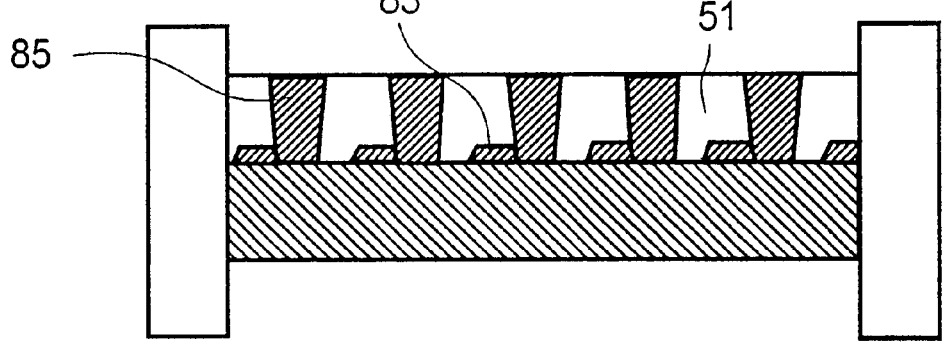
Figure 11:
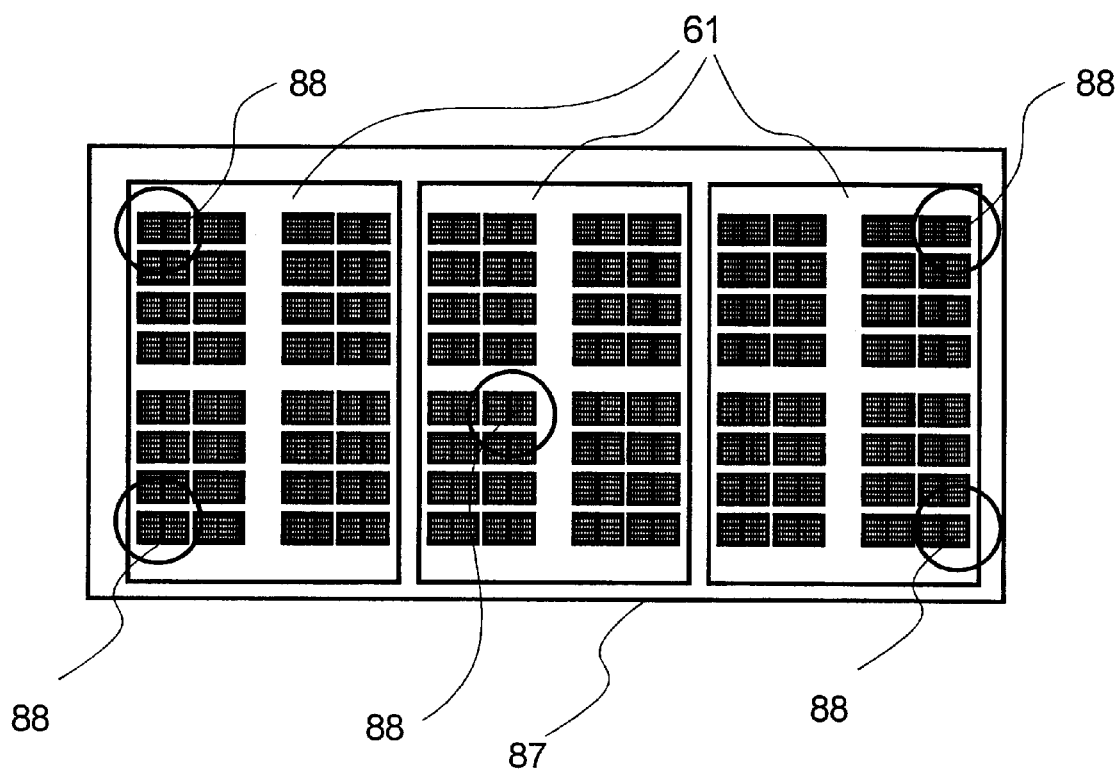
FIG. 11 is a plane view of a wafer showing inspection points within a shot.

FIG. 5 and FIG. 6 have shown examples of failures due to inadequate etching. Other failures such as offset against lower layer patterns and alignment failure due to rotation and scaling at exposure as shown in FIG. 9 and FIG. 10 can also be detected. FIG. 9 shows an example of increased contact resistance between a window pattern and the underlying conductor caused by the alignment failure of a contact window 80 on the first layer and a contact window 82 on the second layer. FIG. 10 shows an example of a short circuit with conductor routing of the lower layer. In addition to inspection of failure distribution within a wafer as shown in FIG. 8, performing a check of five positions (each given reference numeral 88) including four corners and a center within a shot 87 as shown in FIG. 11 is preferable because it enables inspection of alignment failures in a shot. In addition to inspections of these window patterns, characteristics inspection can be performed similarly for whatever with the same pattern repeated, including patterns after windows are filled, resist patterns, and well patterns formed on the substrate.

Figure 12A:
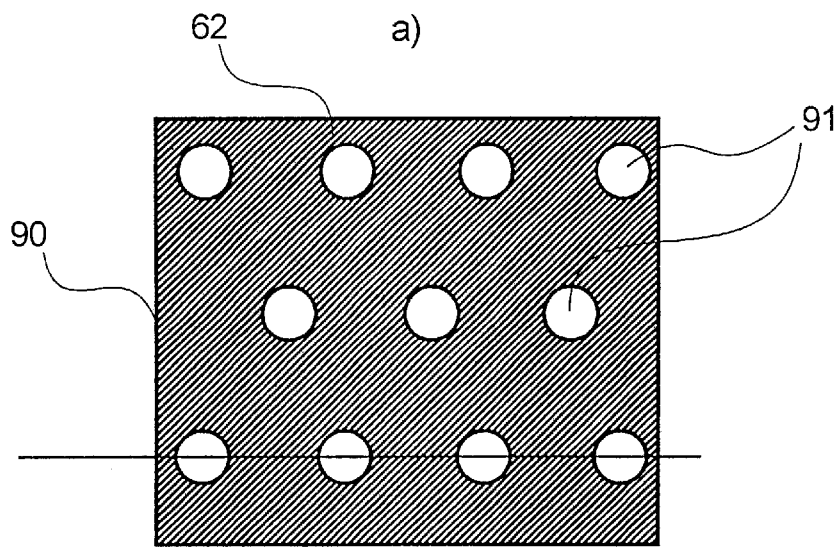
FIG. 12(a) is a plane view of a chip showing a window pattern.
Figure 12B:
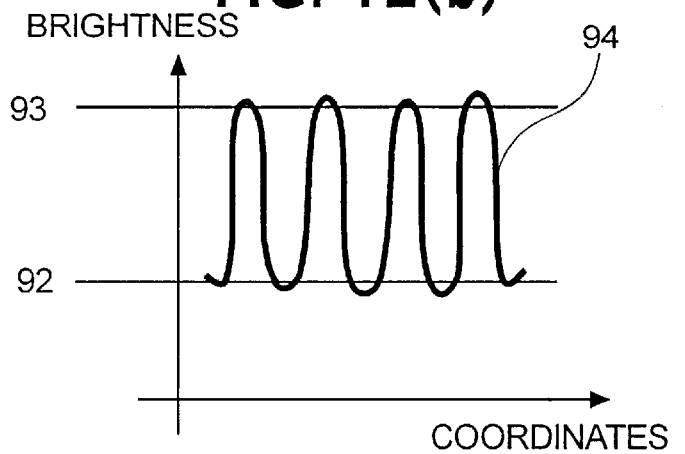
FIG. 12(b) is a graph showing the relationship between the coordinate data within the image and the brightness.
Figure 12C:
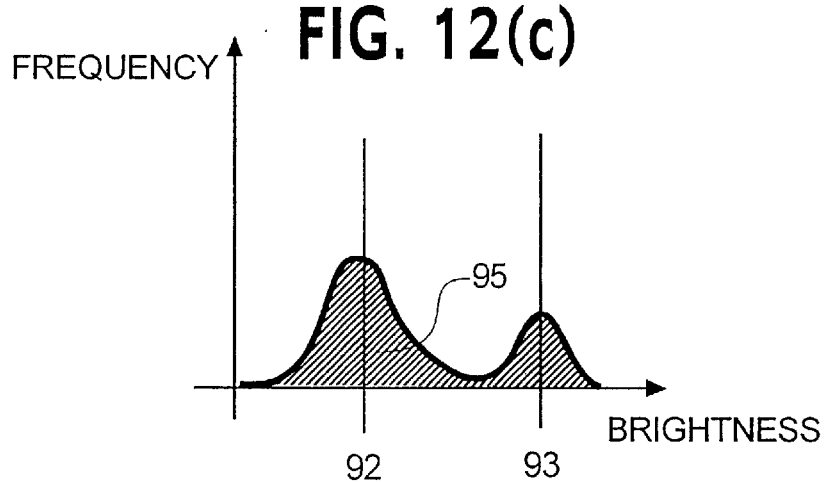
FIG. 12(c) is a graph showing the relationship between the brightness and the occurrence frequency.

Then, referring to FIG. 12 and FIG. 13, an example method of measuring the typical brightness value of each window using these images of patterns. In advance, the average brightness of a groundwork 90 and a window pattern 91 are determined with the help of an image of an normal section. For example, it may be determined at the peaks of a pattern waveform 94 of an image as shown in FIG. 12(b) or with the use of a histogram 95 as shown in FIG. 12(c). A threshold level ThL for image processing is determined from the measurement value of the brightness. The threshold level ThL is determined separately from the control value for evaluating the quality of patterns and is used for identifying the positions of patterns and computing the typical brightness value.

Figure 13A:
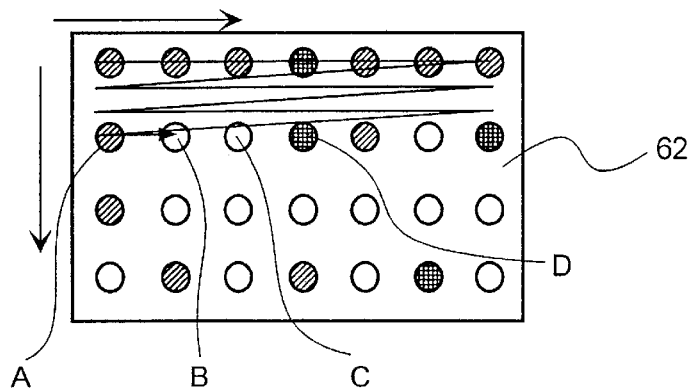
FIG. 13(a) is a plane view of a chip showing a contact window pattern.
Figure 13B:
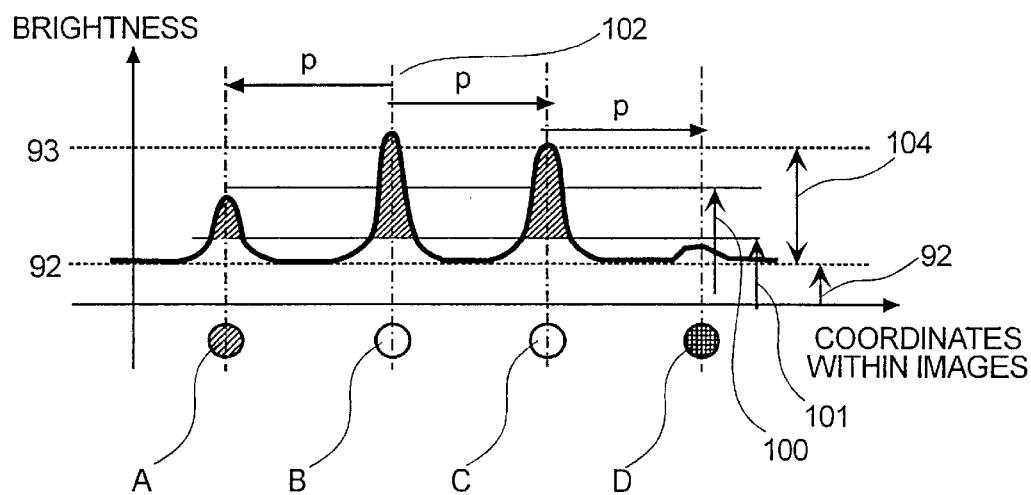
FIG. 13(b) is a drawing showing the relationship between coordinates within the image and the brightness.
Figure 13C:
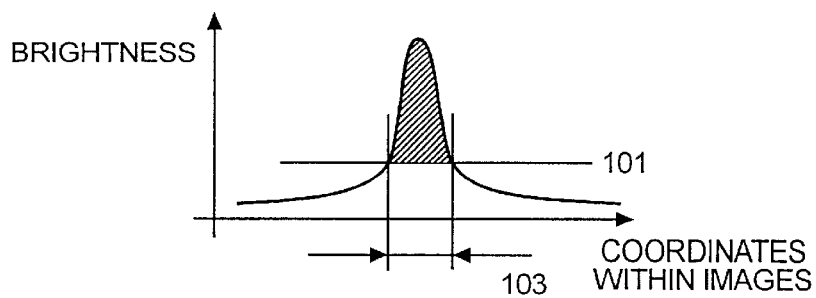
FIG. 13(c) is a drawing showing the relationship between the brightness and the occurrence frequency.

First, as shown in FIG. 13(a), an image 62 of a section to be inspected is scanned sequentially from top left and searched for points over the threshold level ThH 100 to determine the positions of patterns. In FIG. 13, pattern B is detected first. As shown in FIG. 13(b), starting form position 102 of pattern B, patterns in positions at a distance by repetition pitch p of a cell pattern are searched to determine the positions of pattern A and pattern C. Next, the position of pattern D is determined from the position of pattern C. In this way, all pixels within the image 62 are searched for in the X and Y directions to determine positions of patterns within the image. Where, calculation of the positions can be determined as the center position of gravity of the area over the threshold level 100 as show in FIG. 13(c).

The positions are determined with the use of the threshold level for the propose of obtaining higher reliable position information with the use of an image of a bright-enough point. If there are no bright-enough points in the threshold level, an image of the brightest point in the image may be used. If a pattern is less bright as pattern D as shown in FIG. 13(b) and the brightness around the position of the pattern to be searched for is below a threshold level 101, this pattern can be determined as a failed pattern and the next pattern is checked.

After all pattern positions are determined, a typical brightness value of each pattern is calculated. This can be an average value of brightness of points over the threshold level ThL 101, or a value determined by calculating the sum of brightness of these points and dividing it by a number of pixels 103.

Repetitive pitch p of a pattern used for calculating positions can be indicated by an operator 128 in advance, or can automatically be calculated from the design data.

As is evident from above, the threshold level ThL 100 for image processing is a threshold for detecting a point of a pattern in reliability, which can be determined, for example, by adding the brightness of the groundwork 92 to the brightness of about 70 percents of amplitude of a pattern 104. In contrast to this, the threshold level ThL 101 is used for determining the presence or absence of patterns, which can be determined, for example, by adding the brightness of the groundwork to the brightness of 10 to 20 percents of amplitude of the pattern 104. FIG. 13 illustrates the case where a pattern is brighter than the groundwork, which is shown in white color for easier to understand. Although patterns can be inversed depending on electronic optical system parameters, application of the methods shown in FIG. 12 and FIG. 13 to that case enables evaluation of the brightness of a pattern.

In addition, the same effect can be expected as in the case of using the typical brightness value when evaluation of the brightness of a pattern with the use of the number of pixels of brightness of a range beyond the threshold level as a parameter indicating the dimension of the pattern instead of a typical brightness value as shown in FIG. 13(c).

Figure 14A:
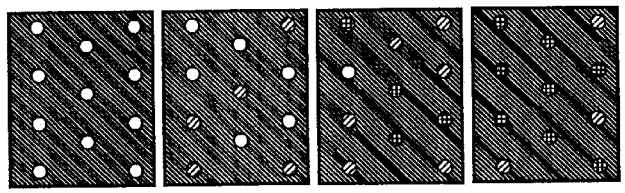
Figure 14A:
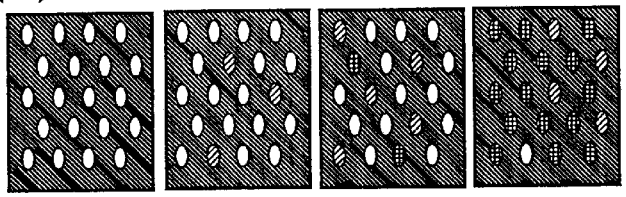
Figure 15A:
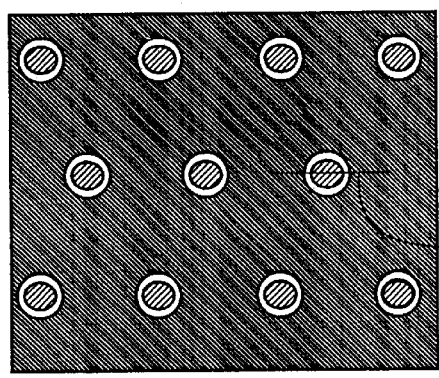
FIG. 15(a) is a plane view of a semiconductor chip showing a contact window pattern.
Figure 15B:
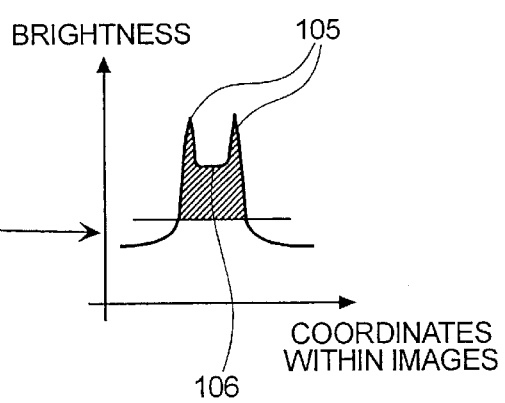
FIG. 15(b) is a drawing showing the relationship between the coordinates within the image and the brightness.

As shown in FIG. 14(b), if a pattern density is high and the ratio of the area occupied by patterns to the groundwork is high, there is no need to measure the typical brightness value of each pattern. Similar effect is obtained by evaluating the average brightness value over an entire image and variations. In this case, since calculation amount for image processing is smaller than that for the example mentioned above, faster inspection is possible.

Furthermore, if the resolution of an electronic optic system is high, it is observed that a pattern edge 105 outshines the pattern because of so called a white edge effect. In this case, it would be possible to calculate the typical brightness value as in the case of FIG. 13. As is the case with the example of FIG. 13, evaluation using the brightness only within a pattern would also be possible with the use of the image around a pattern center 106 after calculation of pattern positions and by processing around the white edge parts through edge detecting operation. When the white edge parts are very bright, background noise can be reduced through these operations and subtle variations of the brightness within the pattern can be determined.

In this way, typical brightness values of repetitive patterns can be calculated through image processing. However, for patterns on products, surface potentials when irradiated by electron beams vary and signal amount of a secondary electron beam image to be obtained varies depending on distribution of impurities in the substrate, the presence or absence of p-n junctions in the substrate, and difference in methods of interconnection to other regions of traces.

Figure 16A:
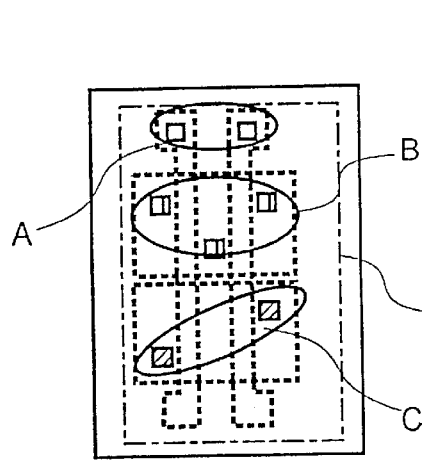
FIG. 16(a) is a plane view of a semiconductor chip showing the layout of contact windows.

For example, on forming contact windows shown in FIG. 3 through the process of a device shown in FIG. 1, contact conditions between the contact windows and underlying conductors formed in a unit cell for connection to a trace are different among groups A, B and C shown in FIG. 16(a). Therefore, image processing allowing for the difference of brightness of these patterns is required. For this purpose, a unit cell area 110 is set as shown by a dotted line, the positions of patterns within the unit cell area 110 are registered in advance. For example, the top left coordinates of the unit cell area 110 are set as an origin 111 and the coordinates of each pattern 112 can be registered based on it. This registration may be done through mouse operation by an operator when checking the image, or may be made from the design data automatically. All or some of these patterns with the coordinates registered can be used to perform evaluation by pattern type similar to that in the case of FIG. 6.

To determine pattern positions, operations such as ordinary template-matching may be used. As shown in FIG. 16(a), for example, a pattern of the unit cell area 110 that has been obtained in a normal section is stored as a template image 113, a pattern 114 corresponding to the template image 113 is detected within a range of repetitive cell pattern pitch, and, subsequently, similar patterns are searched for around the coordinates at a distant of a pattern pitch pp. At this time, if an obtained image and the pattern of the template image 113 have a low correlation value, the brightness within the obtained image is evaluated to determine the presence or absence of patterns. For example, if only the brightness of the same level as that of the groundwork exists, it can be determined that the peripheral area is faulty. If the position of a unit cell can be determined, pattern positions within the unit cell can easily be determined on the basis of the coordinates that have been registered in advance.

Since many other possible methods for identifying pattern positions and measuring typical values exist, an appropriate image processing method can be used as the case may be.

Next, A method of determining the threshold level ThL 68 for evaluating the quality of a pattern in the inspection using the brightness of a charged particle beam image of the invention will be described. As another embodiment of the method (shown in FIG. 7) for determining the threshold level ThL 68 using the relationship between the brightness measured in advance and resistance values, there is A method of determining the inspection threshold level at the time of proposition of the production parameters.

Usually, when a new product is introduced into a production line, production parameters are proposed. For instance, in the case of exposure apparatus, parameters including exposure time, focus offset, alignment with lower layers, and rotating amount are defined, then used to expose patterns practically, and adjusted to the best parameters depending on the result. For etching, processing conditions are set by changing gas to be used and etching time.

Figure 17:
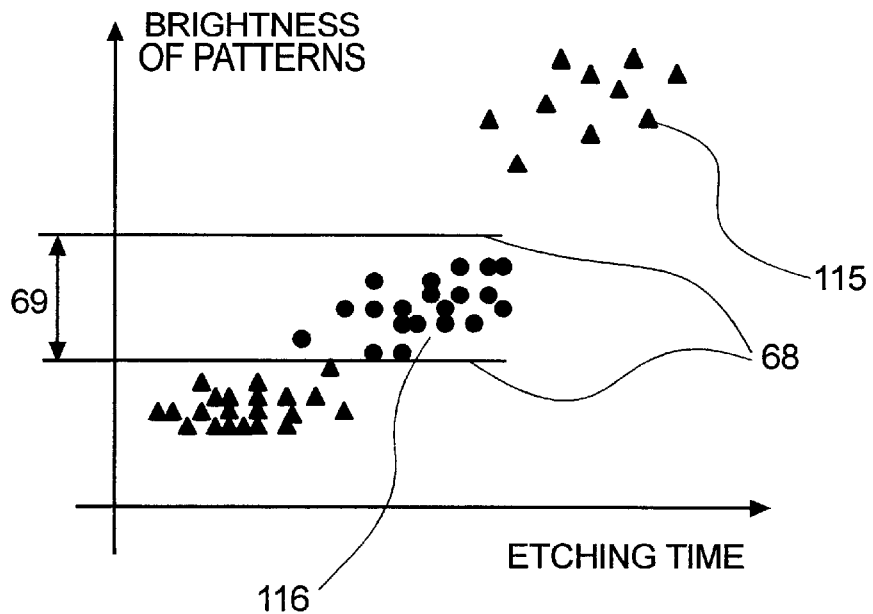
FIG. 17 is a graph showing the relationship between etching time and the brightness of a pattern.

At this time, in-depth checks are performed by using critical dimension measurement SEM combined with visual checks for cross sections as required. A method of evaluating the image of a formed pattern at this time and determining the evaluation value will be described. For example, if the sample image for proposition of production parameters generated by changing etching time is obtained and evaluated, and the result of the quality evaluation is plotted with the evaluation, the graph as shown in FIG. 17 is obtained. In this way, if the relationship between the result of quality evaluation and the typical brightness value can be obtained, the control value 68 corresponding to a typical brightness value can be determined. In the example shown in FIG. 17, a pattern that has been evaluated as faulty is indicated with a triangular mark 115 and a pattern that has been evaluated as normal is indicated with a round mark 116. From the result of this quality evaluation and the measuring result of a typical brightness value, a brightness tolerance 69 of a normal pattern can be determined and the control value used in FIG. 6 can be determined.

FIG. 17 shows an example of proposition of etching time parameters. At the time of proposition of other process parameters, control values can be determined similarly if the image feature amount of a normal section and a failed section can be obtained.

Figure 18:
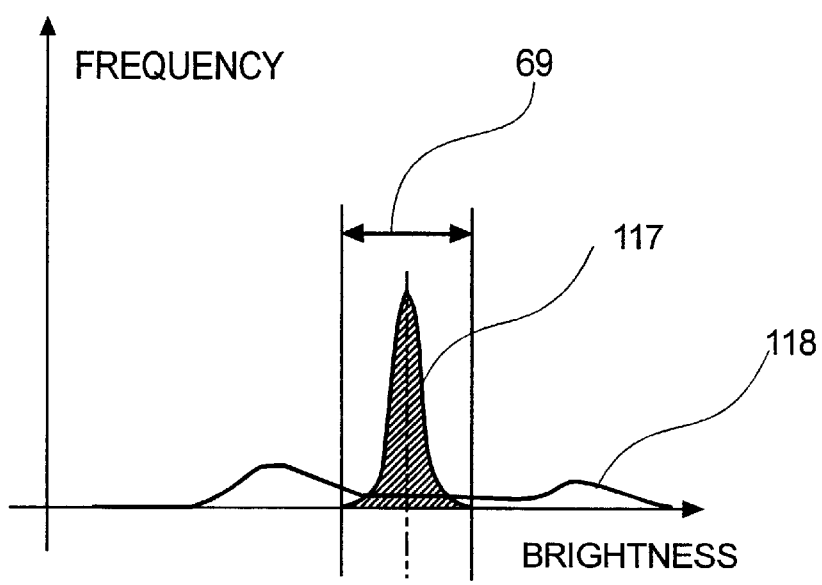
FIG. 18 is a graph showing the relationship between the brightness and the occurrence frequency.

Next, an example of another control setting method will be described by referring to FIG. 18. In a production process of semiconductor devices, operation checks of completed devices are performed before shipping. The control values for inspection can also be determined with the use of the result of quality evaluations at this time. For example, an inspection image is obtained at a certain stage before being matched to the result of the fail-bit analysis for the resulting produced device. As shown in FIG. 18, distribution of the typical brightness value of normal bits 117 is obtained, which can be used to determine the control value. In FIG. 18, failures occur at bit having the same typical brightness value of a normal section, because failures might occur at stages other than the stage of interest.

Figure 16B:
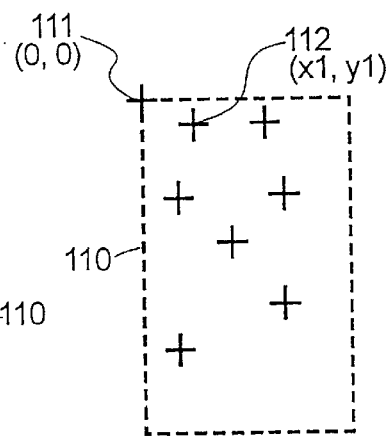
FIG. 16(b) is a plane view of a semiconductor chip showing the center coordinates of each of the contact windows.
Figure 16C:
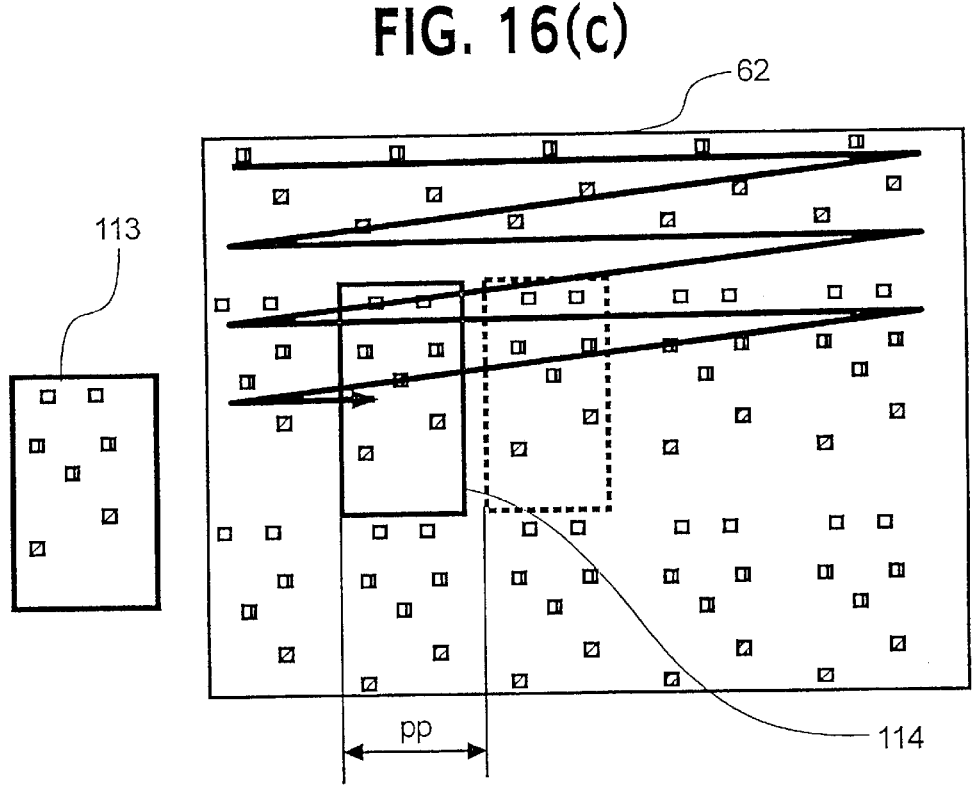
FIG. 16(c) is a plane view of a semiconductor chip showing the state of electron beam scanning on it.

Since the brightness control value 68 used in FIG. 6 varies according to irradiation parameters including the acceleration voltages of electron beams and beam current, it is required to determine it separately by inspection apparatus to be used. If mixed kinds of patterns exist as shown in FIG. 16, a plurality of control values should be set for each pattern group in which each pattern within a unit cell is the same or has the same geometry and characteristics, or only a certain pattern within a unit cell or pattern groups with the same geometry and characteristics should be evaluated.

Figure 19:
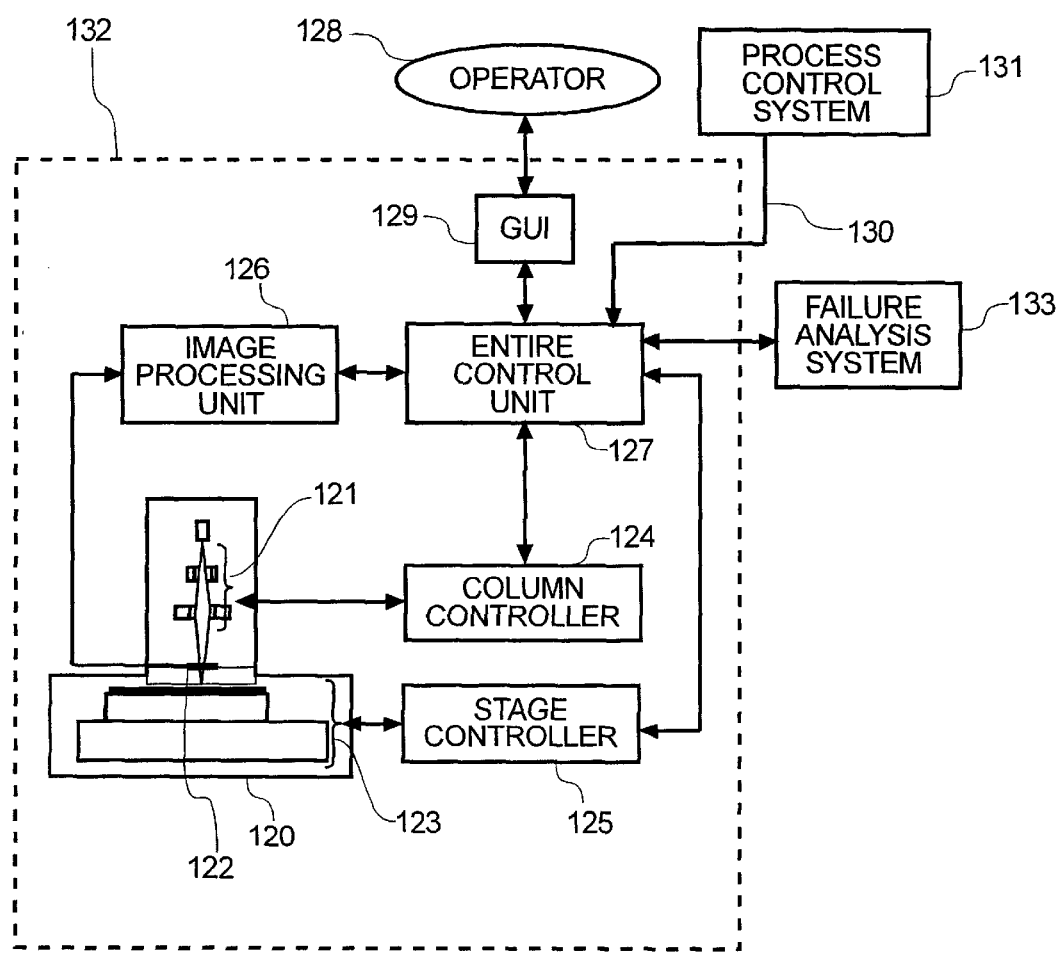
FIG. 19 is a schematic plane view of the inspecting system showing an embodiment of the invention.
Figure 20:
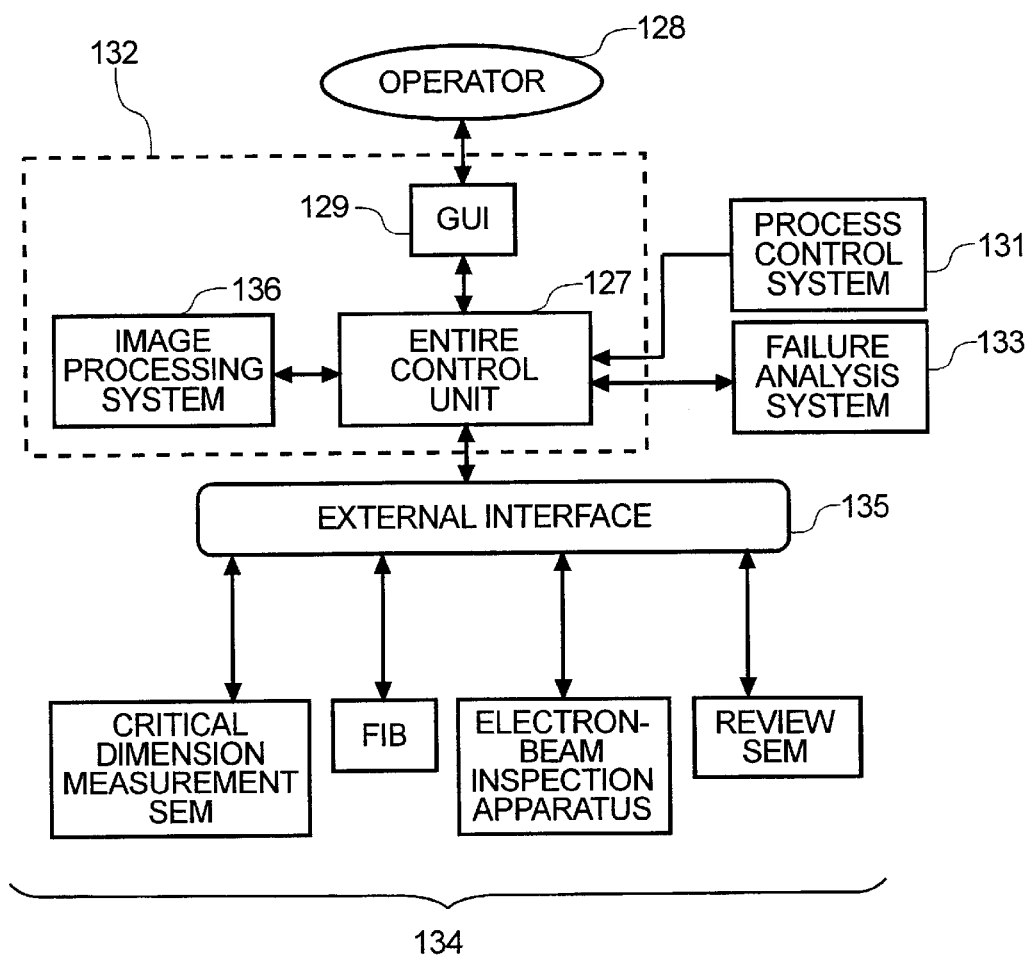
FIG. 20 is a schematic front view of an inspection system showing another embodiment of the invention.

Next, A method of implementing an inspection system 132 carrying out these inspections will be described. FIG. 19 shows an example of an inspection system of this invention. A mainframe of an inspection apparatus 120 consists of an electron optics system 121 for building up SEM images, a detector 122 for detecting secondary electron images, and an X-Y stage 123 for holding specimens and enabling observation of desired positions. A column controller 124 can adjust parameters such as the acceleration voltages and current of irradiating beams and focusing positions to obtain excellent inspection images. A stage controller 125 can shift the X-Y stage 123 to a desired position to perform inspection image processing for the images that have been detected by the detector 122 at an image processing unit 126. These are controlled by an entire control unit 127 and can perform inspection operations as shown in FIG. 6.

The operator 128 can easily specify inspection areas and display the inspection results on a GUI display 129. The entire control unit 127 provides a function for receiving a working history 130 of a wafer to be inspected (information about the fabricating equipment and working time) from a process control system 131 and analyzing the inspection results. The entire control unit 127 is also connected to a failure analysis system 133 and can receive the test results of inspected wafers and the results of their fail-bit analysis.

The following shows an example of A method of preparing an inspection recipe. First, an item to be inspected and process are selected and inspection parts within a wafer, shot, or chip are decided. At this time, if failure-prone parts for production equipment are known, they should be specified as areas to be inspected without fail. Next, electron beam images of normal sections are obtained in practice to determine the pattern brightness of the normal sections and the brightness of the groundwork. At this time, the repetitive pitch of the cell pattern and compound patterns as shown in FIG. 16 are set. Finally, the control value is determined by the methods mentioned above.

If a charged particle beam unit 134 has a function for obtaining images at desired positions within a wafer as ordinary SEM and FIB, it would be possible to implement applications with many kinds of charged particle beam units by connecting to an external interface 135 for sending image obtaining commands and transferring obtained images to an image processing unit 136 capable of processing images and displaying the results.

Next, a feedback method from the results to the production process of the invention will be described. Although it is easy to determine a process in which a failure occurs if inspections are carried out at completion of each process shown in FIG. 4, it is practically difficult to perform inspection at all the processes.

For example, suppose an inspection is performed only after resist stripping at process n and process n+1. It would be impossible to determine at which stage, from cleaning stage at process n to resist stripping stage at process n+1, failures detected after resist stripping stage at process n+1 have occurred. In this case, if there is a function for displaying inspection results specific to commencement equipment at every stage from the cleaning stage at process n to the resist stripping stage at process n+1, it would increase the possibility of obtaining information beneficial to the identification of the equipment causing the failures.

Figure 21A:
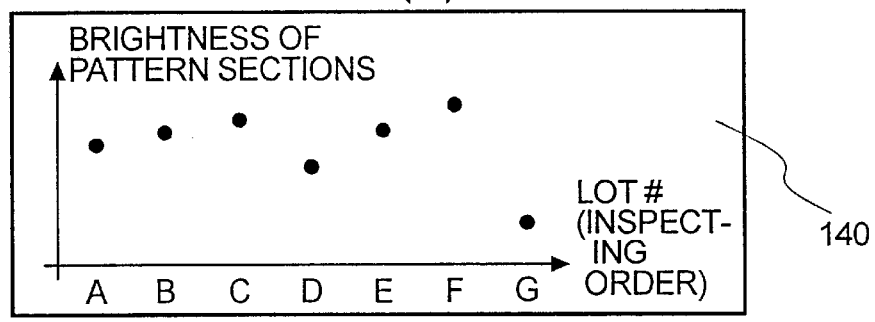
FIG. 21(a), FIG. 21(b), and FIG. 21(c) are drawings all showing the relationship between the typical brightness values during inspection time and time and date of commencement.

For example, the relationship between the typical brightness value and the time and date of commencement as shown in FIGS. 21(a), (b), and (c) can be displayed for each commencement equipment at each time and date of commencement. (In FIG. 21, information about an item operated upon equipment A is plotted in (b), and information about an item operated upon equipment B is plotted in (c). Comparing the data of FIG. 21(b) to the data of FIG. 21(c) makes it clear that the performance of equipment B has gradually been exacerbated. It is impossible to recognize the fact from the data for items only put into the inspected order as shown in FIG. 21(a), and makes it easy to identify equipment that caused the failures.

Figure 21B:
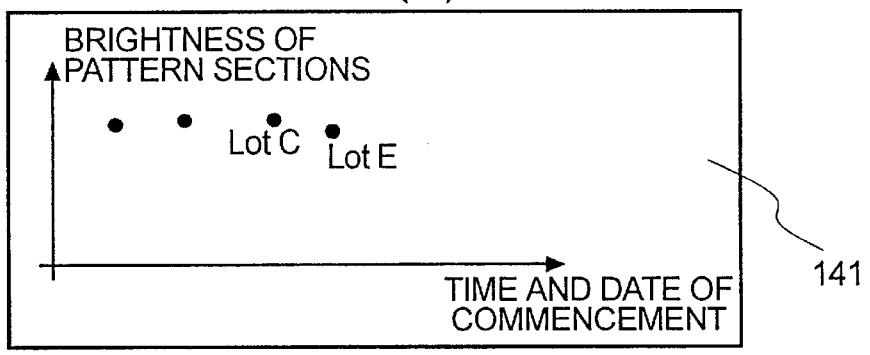

FIG. 21 shows a typical brightness value per lot for simplicity, but the number of the typical brightness values is not limited to one, and the horizontal axis may be set in a unit of wafer. For the inspection on a plurality of points within a wafer, the mean value and the minimum value of the brightness or all inspection results may be displayed at the same time. This method enables inspections in shorter time, or a few minutes per wafer, in comparison with ordinary inspection apparatus using electron microscope, so, if the frequency of spot checks is increased, further reliable results reflecting equipment conditions will be obtained. If it is programmed in such a way that the time series data of the inspection results as shown in FIGS. 21(b) and (c) is automatically accumulated and that alarm is given when the data falls below a reference level or when it abruptly varies, it would be possible to control process changes.

Figure 21C:
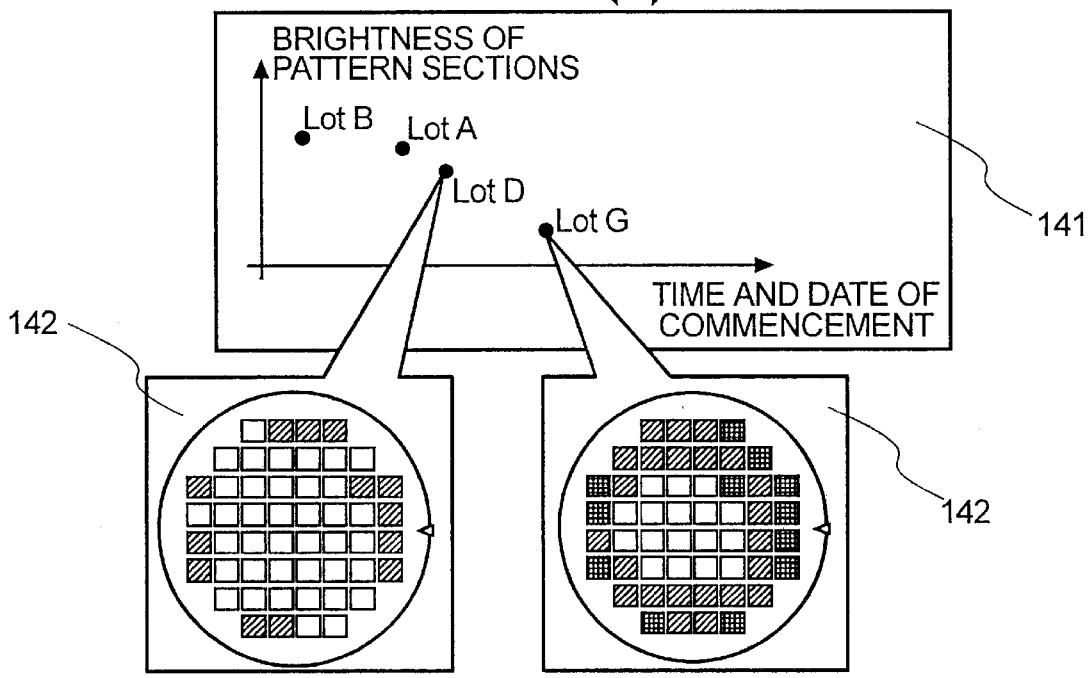

If distribution of failures within a wafer surface 142 as shown in FIG. 21(c), as well as the distribution of failures within a shot are displayed, it would make it easier to assume problem equipment. In general, information of manufacturing equipment and working time is controlled on production lines and the data can be available when necessary. If it is recognizable in advance that the typical brightness value of a pattern is gradually going down as shown in an example of FIG. 21(c), it would be possible to prevent occurrence of failures by carrying out maintenance of equipment parts previously. In examples shown in FIG. 21, the vertical axis of each graph indicates the typical brightness value of patterns but may indicate the occurrence probability of failed patterns or normal patterns that has been estimated by a method in FIG. 6.

The invention makes it possible to keep track of failure occurrence conditions on an entire wafer of interest only by inspecting minimum area, thereby implementing fast inspection and enabling its in-line usage. In addition, the invention makes it possible to prevent mass occurrence of failures due to defective conditions of manufacturing equipment by controlling change in processes.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method of fabricating a semiconductor device, comprising the steps of:

(a) detecting a secondary electron image of a partial area of a wafer which has been processed by a processing apparatus by irradiating and scanning an electron beam onto the partial area of the wafer and detecting secondary electrons emitted from the wafer by the irradiating and scanning;

(b) estimating failure occurrence conditions in areas other than the partial area of the wafer by using the detected secondary electron image;

(c) storing data regarding the estimated failure occurrence conditions associated with information regarding the processing apparatus and a date when the wafer was processed;

(d) sequentially performing the steps (a) to (c); and (e) observing failure occurrence conditions of the processing apparatus by monitoring time-varying conditions of the data stored in the step (c).

2. A method of fabricating a semiconductor device according to claim 1, wherein the processing apparatus is an etching apparatus.

3. A method of fabricating a semiconductor device according to claim 1, wherein the step of estimating failure occurrence conditions in areas other than the partial area is performed by using statistical data of the secondary electron image of the partial area of the wafer.

4. A method of fabricating a semiconductor device according to claim 1, wherein the data regarding the estimated failure occurrence conditions is data regarding a brightness of the secondary electron image.

5. A method of fabricating a semiconductor device according to claim 1, wherein an alarm is issued when a disorder of the time-varying conditions is monitored in the step of observing.

6. A method of fabricating a semiconductor device, comprising the steps of:
   (a) irradiating an electron beam onto a partial area of a wafer which is one of a plurality of wafers processed by a processing apparatus in a processing line;
   (b) detecting secondary electrons emitted from the wafer;
   (c) detecting a secondary electron image of the partial area of the wafer from the detected secondary electrons;
   (d) estimating failure occurrence conditions in areas other than the partial area of the wafer by using the detected secondary electron image;
   (e) storing data regarding the estimated failure occurrence conditions associated with information regarding the processing apparatus and a date when the wafer was processed;
   (f) repeating the steps (a) to (e); and
   (g) displaying on a screen the stored data in order corresponding to each processing apparatus.

7. A method of fabricating a semiconductor device according to claim 6, wherein the processing apparatus is an etching apparatus.

8. A method of fabricating a semiconductor device according to claim 6, wherein the step of estimating failure occurrence conditions in areas other than the partial area is performed by using statistical data of the secondary electron image of the partial area of the wafer.

9. A method of fabricating a semiconductor device according to claim 6, wherein the data regarding the estimated failure occurrence conditions is data regarding a brightness of the secondary electron image.

10. A method of fabricating a semiconductor device according to claim 6, wherein in the step of displaying, data regarding a distribution of failure occurrence conditions on the surface of the wafer is displayed on the screen.

11. A method of fabricating a semiconductor device according to claim 6, wherein in the step of displaying, the estimated data regarding the failure occurrence conditions is displayed on the screen.

12. A method of fabricating a semiconductor device, comprising the steps of:
   (a) detecting a secondary electron image of a partial area of a wafer which has been processed by a processing apparatus by irradiating and scanning an electron beam onto the partial area of the wafer and detecting secondary electrons emitted from the wafer by the irradiating and scanning;
   (b) estimating failure occurrence conditions in areas other than the partial area of the wafer by using the detected secondary electron image;
   (c) storing data regarding the estimated failure occurrence conditions associated with information regarding the processing apparatus and a date when the wafer was processed;
   (d) sequentially performing the steps (a) to (c); and
   (e) controlling a change of process condition of the processing apparatus using the stored data.

13. A method of fabricating a semiconductor device according to claim 12, wherein the processing apparatus is an etching apparatus.

14. A method of fabricating a semiconductor device according to claim 12, further comprising the step of displaying data regarding the failure occurrence conditions stored in the step of storing.

15. A method of fabricating a semiconductor device according to claim 14, wherein the data regarding the estimated failure occurrence conditions is data regarding a brightness of the secondary electron image.

16. A method of fabricating a semiconductor device according to claim 14, wherein in the step of displaying, a distribution of failure occurrence conditions is displayed.

17. A method of fabricating a semiconductor device according to claim 14, wherein in the step of displaying, data regarding a distribution of failure occurrence conditions on the surface of the wafer is displayed.

18. A method of fabricating a semiconductor device according to claim 14, wherein in the step of displaying, data regarding the estimated failure occurrence conditions is displayed.

* * * * *